(12) United States Patent
Hebert et al.

(10) Patent No.: US 10,042,977 B2
(45) Date of Patent: Aug. 7, 2018

(54) METHOD UTILIZING REPEAT PSA SCREENING FOR DIAGNOSIS OF VIRULENT PROSTATE CANCER

(71) Applicant: UNIVERSITY OF SOUTH CAROLINA, Columbia, SC (US)

(72) Inventors: James R. Hebert, Columbia, SC (US); Azza Shoaibi, Cayce, SC (US)

(73) Assignee: University of South Carolina, Columbia, SC (US)

( * ) Notice: Subject to any disclaimer, the term of this patent is extended or adjusted under 35 U.S.C. 154(b) by 336 days.

(21) Appl. No.: 14/854,371

(22) Filed: Sep. 15, 2015

(65) Prior Publication Data

US 2016/0078171 A1     Mar. 17, 2016

Related U.S. Application Data

(60) Provisional application No. 62/050,453, filed on Sep. 15, 2014.

(51) Int. Cl.
*G01N 33/48* (2006.01)
*G06F 19/24* (2011.01)

(52) U.S. Cl.
CPC .................................. *G06F 19/24* (2013.01)

(58) Field of Classification Search
CPC ....................................................... G06F 19/24
USPC ........................................................... 702/19
See application file for complete search history.

(56) References Cited

PUBLICATIONS

Shoaibi, et al., Presentation at Urology Conference; Sep. 20, 2014, 23 pages.

*Primary Examiner* — Jerry Lin
(74) *Attorney, Agent, or Firm* — Dority & Manning, P.A.

(57) ABSTRACT

A method for detecting aggressive prostate cancer is described, for instance for use in determination of the need for biopsy based. Disclosed methods recognize the difference in PSA rate of change for men in different prostate health states and having different risk profiles so as to provide a route for earlier detection of aggressive prostate cancer, for example in asymptomatic men.

12 Claims, 4 Drawing Sheets

METHOD UTILIZING REPEAT PSA SCREENING FOR DIAGNOSIS OF VIRULENT PROSTATE CANCER

CROSS REFERENCE TO RELATED APPLICATION

This application claims filing benefit of U.S. Provisional Patent Application Ser. No. 62/050,453 having a filing date of Sep. 15, 2014, which is incorporated herein by reference in its entirety.

GOVERNMENT SUPPORT CLAUSE

This invention was made with government support under K05 CA136975 and under 1U54 CA153461-01 awarded by the National Cancer Institute. The government has certain rights in the invention.

BACKGROUND

Prostate cancer is a disease with a unique combination of high incidence but low virulence, and therefore represents a major public health challenge in the United States. Population-based screening with a single Prostate Specific Antigen (PSA) test detects mostly low-risk indolent cancers. Diagnosing and treating such low-risk prostate cancer is likely to cause more harm than benefit. The challenge is to improve screening sensitivity and specificity for clinically significant, high-risk prostate cancer so as to be able to preferentially detect cancers that may be clinically lethal; this is an unmet need that is likely to impact quality of life and longevity.

In an attempt to improve PSA-based screening for prostate cancer, researchers have introduced concepts that use multiple serial measures of PSA over time. These concepts are varyingly described as PSA kinetics, PSA growth, PSA rate or PSA velocity (PSAV). Models for determining prostate PSA level change over time have used different assumptions, different statistical methods, and different computational methods. For instance, initial proposals included a multi-phase non-linear model for PSAV computation. Currently, PSAV is derived from linear regression methods or is commonly calculated as the simple average difference of multiple PSA measures.

The totality of the evidence has suggested that known methods for determining PSA kinetics/velocity do not improve prostate cancer detection. Even so, research has shown that on average, the pattern (not just the simple "rate") of PSA increase is quantitatively and qualitatively different in patients with aggressive prostate cancer as compared to men with localized prostate cancer, other prostate disorders (e.g., benign prostatic hyperplasia, prostatitis), and in those men with no known prostate condition.

Studies have reported different PSA change rate with time for cancer patients, probably because each study used a different cohort of men originally selected for a different research question. In addition, studies have not controlled for important confounders. For example, body mass index (BMI, a measure of relative weight that is derived by dividing the individual's weight, in kilograms (kg), by his height, in meters (m) squared, that is used as a proxy for overweight/obesity), race, and prostate volume have not always included in the models. Another limitation to previous studies is the small number of subjects for most of the included studies.

Multiple definitions for PSAV, lack of a single threshold cut-off value for PSAV, and sensitivity of PSA to biological and bio-behavioral characteristics, such as BMI, race, age, medications and smoking has led to confusion and debate as to whether determination of PSAV improves prostate cancer detection. Some evidence supports its use and some argues against it. Nevertheless, there is general consensus that when measured rigorously, PSA change over time differs quantitatively and qualitatively across men who develop prostate cancer versus those who with benign prostatic hyperplasia (BPH) or normal prostates of apparently healthy men. Even among men with prostate cancer, PSA change over time appears to be different for aggressive prostate cancer patients compared to non-aggressive cancer.

What is needed in the art is a method for determining and utilizing the PSA rate of change to detect aggressive prostate cancer and differentiate from other conditions that are less lethal but may be associated with an elevated PSA measure. It would be of great public health and medical benefit if there were a method for detecting aggressive prostate cancer in asymptomatic men that can be utilized to determine whether or not cancer treatment and/or more invasive diagnostic procedures, such as biopsy, should be carried out.

SUMMARY

According to one embodiment, disclosed is a method for detection of aggressive prostate cancer, for instance in an asymptomatic subject. For example, a method can determine a PSA rate of change that is individualized for a particular asymptomatic subject so as to better determine the probability of that subject having an as yet undiagnosed aggressive prostate cancer. Depending upon the PSA rate determination, further treatment or intervention can be carried out. For instance, upon determining that the individual's PSA rate of change exceeds a given threshold value (which can also be individualized based upon a risk profile of the subject), a biopsy can be carried out. Alternatively, should the individual's PSA rate of change be at or below the threshold level, the individual can be merely monitored.

A method can include obtaining three or more PSA levels from the subject, generally with each PSA level being obtained about six months or more apart from one another. The method also includes generating reference growth curves for the different possible prostate health scenarios (non-cancerous, low aggressive cancer, high aggressive cancer) that are individualized for the subject based upon that subject's risk profile. Utilizing the individual's PSA levels, two different PSA/time relationships are then modeled, one based upon a linear PSA growth curve and one based upon an exponential growth curve. A standard regression analysis is then carried out to determine the best fitted model, e.g., by use of an R-squared measure (which quantifies overall explanatory ability of the model), so as to determine which of the reference growth curves best fits the individual's PSA levels.

Once the best PSA/time relationship model (linear or exponential) has been determined for that individual, the PSA rate for that individual is obtained through determination of the derivative of the best fitted model and estimation of unknown parameters through the linear regression model using well-established statistical processes. This individualized PSA rate can then be compared to a standard threshold (which varies depending upon the individual's risk profile) to determine the necessity of further treatment/intervention.

BRIEF DESCRIPTION OF THE FIGURES

A full and enabling disclosure of the present invention, including the best mode thereof, directed to one of ordinary skill in the art, is set forth in the specification, which makes reference to the appended figure, in which.

DETAILED DESCRIPTION OF THE INVENTION

Figure 1:
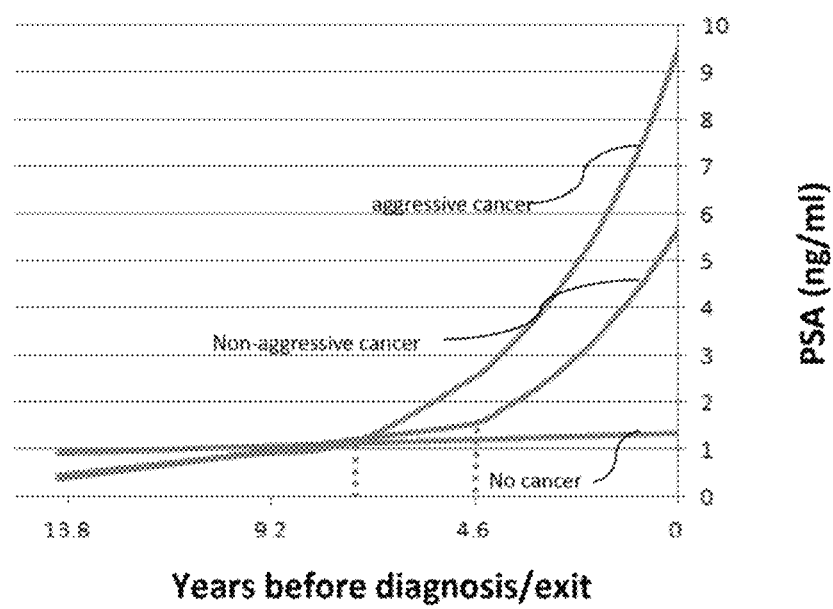
FIG. 1 illustrates the mean PSA growth curve among non-African-American men in the age group of 50-55 years with a BMI of 25 kg/m² or higher that began the study with a PSA of 0.99.

The following description and other modifications and variations to the present invention may be practiced by those of ordinary skill in the art, without departing from the spirit and scope of the present invention. In addition, it should be understood that aspects of the various embodiments may be interchanged in whole and in part. Furthermore, those of ordinary skill in the art will appreciate that the following description is by way of example only, and is not intended to limit the invention.

In general, disclosed herein is a method for detecting aggressive prostate cancer in asymptomatic men and determining the need for biopsy based upon this detection. More specifically, disclosed methods recognize the difference in PSA rate of change for men in different prostate health states and having different risk profiles provides a route for earlier detection of aggressive prostate cancer in asymptomatic men.

The method is based on advanced statistical methods (growth curve analysis) to determine PSA rate of change using at least three PSA concentration levels taken at different times. In addition, individualized reference growth curves are generated based upon the individualized risk profile. The individual's PSA levels are then best-fitted by use of statistical analysis to determine which of the possible growth curve scenarios that individual is on (no cancer, non-aggressive cancer, or aggressive cancer) and thereby provide a more accurate determination of PSA rate of change in that individual.

The three or more successive PSA level concentrations can generally be obtained about six or more months apart, for instance from about six months apart to about three years apart. For example, the method can utilize three or more yearly PSA screening results. Of course, the times between the successive PSA concentration measures do not need to be the same and various timings between measures can be used.

In order to better focus the PSA rate of change determination and ultimate diagnosis to the subject, individualized reference growth curves can also be generated based upon additional factors such as, and without limitation to, race, age, body mass index (BMI), other health considerations (high blood pressure, smoking, diabetes, etc.), etc., to detect early stage aggressive prostate cancer in a subject. For instance, as prostate cancer is known to be more common and virulent in African-American men, according to one embodiment, the individualized reference growth curves that are generated in the method as well as the threshold comparison value for the PSA/time rate of change determined by the process can take self-reported race information into account.

Beneficially, through utilization of the disclosed methods, an individual's change in PSA levels over time (in magnitude and/or direction) can be analyzed based upon the individual's risk profile in conjunction with historical data that has also been partitioned based upon the individual's risk profile to differentiate "high-risk" or "aggressive" prostate cancer from other conditions that could be related to an increased PSA measure at any particular point in time and across different populations. Moreover, the methods can be utilized with asymptomatic men so as to recognize and institute treatment for aggressive prostate cancer earlier that has been possible previously. As utilized herein, aggressive prostate cancer is that which based on tissue evaluation through biopsy and/or surgical samples meets one or more of the following criteria: PSA level ≥20 ng/ml, cancer that invades prostate capsule, cancer that involves more than one lobe, or Gleason score >7 ng/ml.

Studies leading to development of the disclosed methods, described at more length below in the Example section, have found that men with high-risk prostate cancer have a PSA growth curve profile that is distinctly different than that of other conditions and that appears starting as early as 5 to 2 years prior to date of diagnosis. For instance, FIG. 1 presents the mean growth curve for non-African American men of 50-55 years of age, a BMI of 25 kg/m² or greater and a starting PSA level of about 0.99. As can be seen, the PSA level for aggressive prostate cancer cases begins to increase much earlier and with a higher growth rate as compared to low-risk, non-aggressive type cancers and no cancer cases. As such, men in the high-risk cancer group can have a higher absolute PSA rate one year prior to diagnosis, while the range of values among men in the other two groups can vary less or even overlap. However, the absolute PSA rate will not, by itself, provide high levels of confidence in diagnosis, e.g., high enough confidence to go forward with biopsy or cancer treatment. As such, the disclosed methods can utilize the determination of PSA levels over the course of multiple screenings in combination with in combination with an individualized risk profile to confidently diagnose high-risk prostate cancer in asymptomatic men. For instance, utilization of disclosed methods can lead to the establishment of visual/graphical nomograms which can aid biopsy decisions and successfully distinguish virulent prostate cancer from indolent prostate cancer.

As illustrated in FIG. 1, the growth curves for PSA concentration over time are strongly influenced by the presence and type of prostate cancer. Furthermore, the impact of the type of prostate cancer on the growth curve may occur in a window of up to 10 years prior to clinical diagnosis/presentation of the cancer using traditional diagnosis methods.

Figure 2:
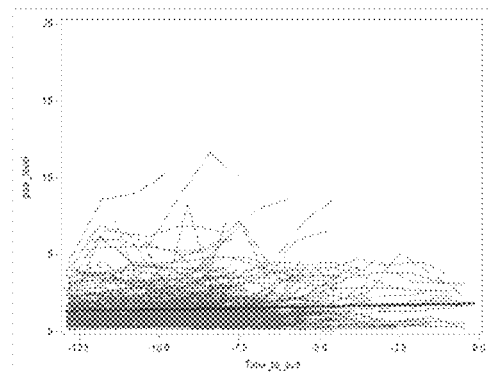
FIG. 2 presents the longitudinal trajectory of PSA levels as a function of time for all subjects with no evidence of prostate cancer.
Figure 3:
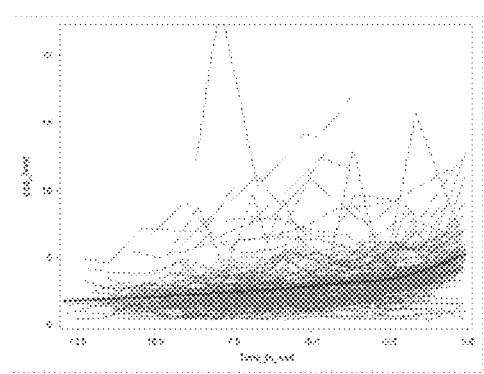
FIG. 3 presents the longitudinal trajectory of PSA levels as a function of time for all subjects with low-risk prostate cancer.
Figure 4:
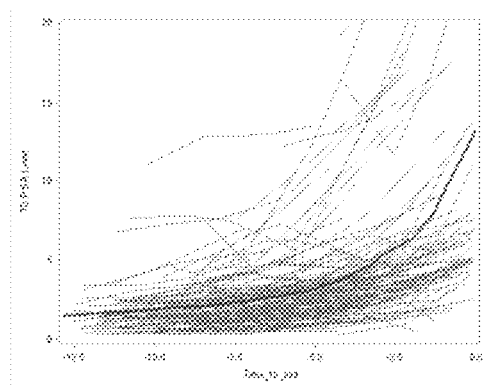
FIG. 4 presents the longitudinal trajectory of PSA levels as a function of time for all subjects with high-risk prostate cancer.

Research leading to development of the disclosed methods also has determined that among men with prostate cancer, there is a transition point at which the PSA level begins to accelerate. For example, FIG. 2, FIG. 3, and FIG. 4 illustrate the longitudinal trajectories of PSA levels in men with no prostate cancer (FIG. 2), low-risk, non-aggressive prostate cancer (FIG. 3), and high-risk, aggressive prostate cancer (FIG. 4). As can be seen in these figures as well as in FIG. 1, there is an inflection point on the graphs at which point the rate of change of PSA levels dramatically increases (e.g., at 7.4 years prior to diagnosis for high-risk cancerous men in FIG. 1, and at 4.6 years prior to diagnosis for low-risk cancerous men in FIG. 1). While not wishing to be bound to any particular theory, it is believed that this inflection point represents a transition (change point) from slow benign and gradual increase of prostatic epithelial volume due to e.g. aging, other prostatic conditions (BPH) to a point at which a malignant tumor is initiated, is still "small," but may have attained the aggressiveness needed to break the basement membrane/prostate capsule—leading to increased 'PSA leakage'.

Also evident in the figures is that in prostate cancer cases of all types, the PSA growth curve is composed of 3 segments including a linear stage, a gradual transition stage, and an exponential growth stage. Beneficially, the disclosed methods can allow for individual variation and be utilized to more accurately diagnose an individual by use of an individualized risk profile that can incorporate a variety of different factors in conjunction with multiple PSA levels of the individual to provide a more confident diagnosis. For instance, by use of the disclosed methods, it can be clear that a given individual can remain in the linear phase or only fit the slower exponential phase and as such need not be subjected to more invasive testing or treatment. However, in those cases in which the method indicates that the probability of high-risk cancer is high, a more aggressive approach, for instance including a biopsy and/or traditional prostate cancer treatment as is generally known in the art, can be carried out.

Figure 5:
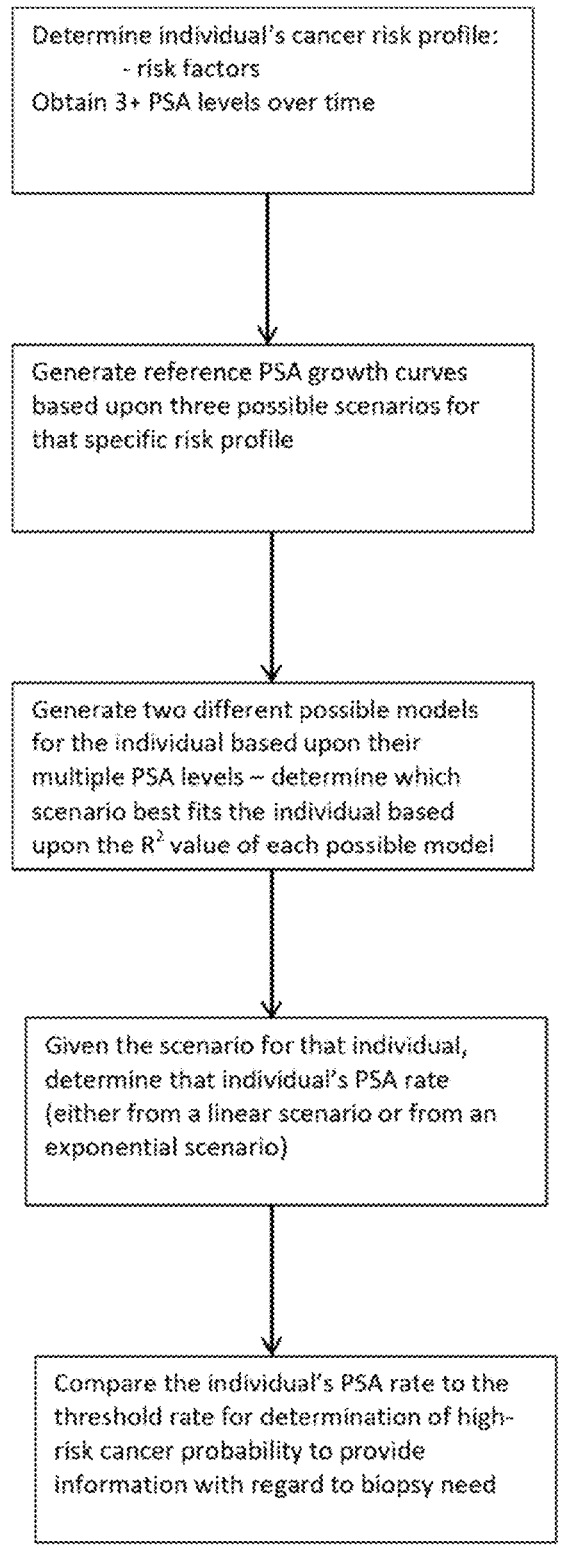
FIG. 5 is a flow chart describing a method as described herein.
Figure 6:
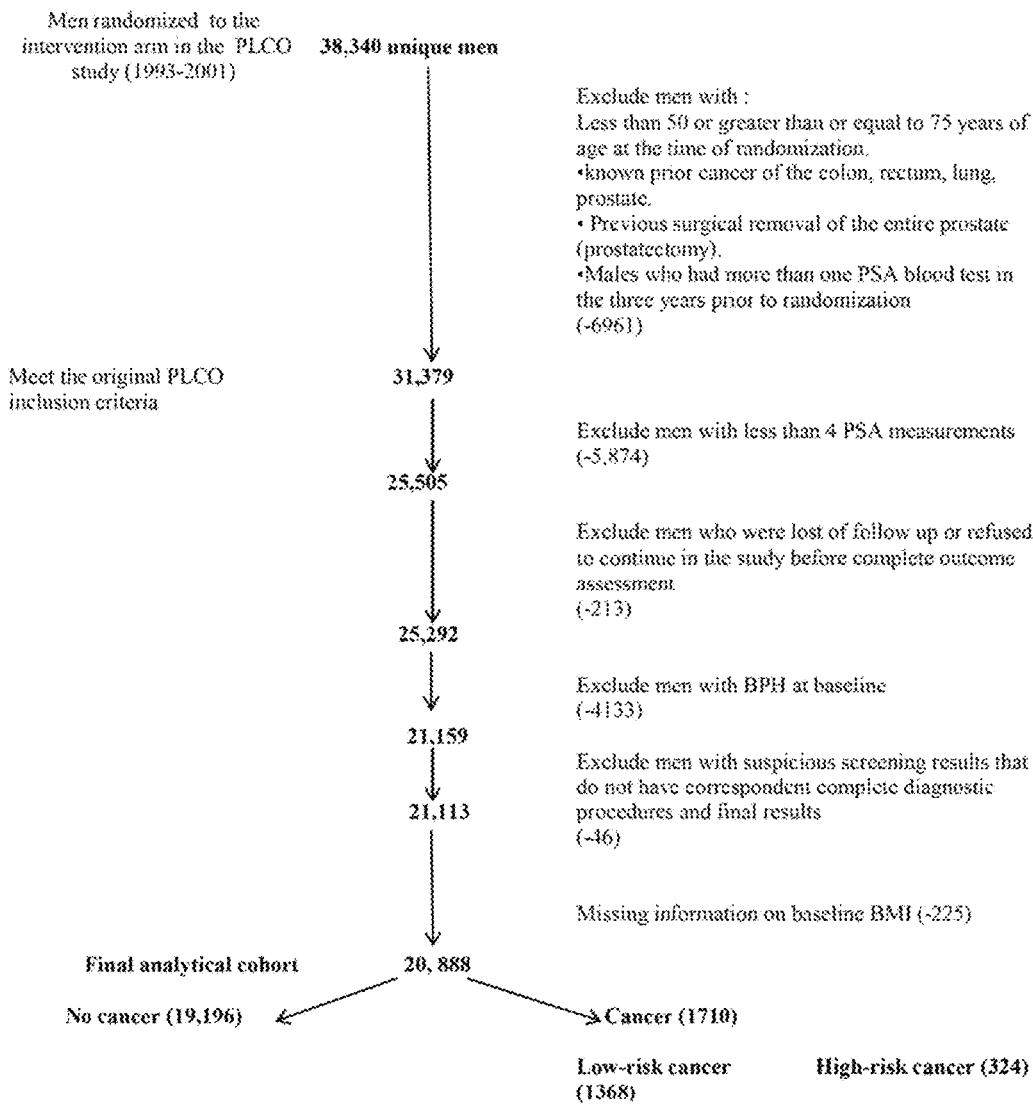
FIG. 6 is a cohort selection tree utilized in the Example described herein.

FIG. 5 presents a flow chart for a process as may be utilized for early diagnosis of aggressive prostate cancer in men, and in one embodiment in asymptomatic men. As can be seen, a method can initially include the determination of a cancer risk profile as well as obtaining multiple (three or more) PSA levels over time. The risk profile can incorporate various lifestyle, genetic, and/or health factors that are known to play a part in the probability of an individual developing aggressive prostate cancer. For instance, it is generally accepted that African-American men are at a higher risk of developing aggressive prostate cancer and of developing prostate cancer at an earlier age (e.g., less than about 50 years of age) as compared to men of other racial backgrounds. Similarly, men having a higher BMI (e.g., about 30 kg/m² or above) are known to be at higher risk for developing aggressive prostate cancer as compared to men having a lower BMI.

Utilizing the risk profile and historical data, reference PSA growth curves can be established for each possible scenario for the individual. In general, three difference reference PSA growth curves can be established: one for a non-cancer scenario (e.g., similar to that illustrated in FIG. 2), one for a non-aggressive cancer scenario (e.g., similar to that illustrated in FIG. 3), and one for an aggressive cancer scenario (e.g., similar to that illustrated in FIG. 4).

Specific functions for each of the three different scenarios have been developed as follows:

Non-Prostate Cancer Reference PSA Growth Curve:

$$PSA_j = 0.7 + (0.07*R) + (0.07*A1) + (0.11*A2) + (-0.03*B) + (0.85*PSA_i) + [(0.05 + (0.01*R) + (0.1*A2))*(X)]$$

In which:
PSA$_j$: represents PSA measure at a certain time point.
R: represents the race of the subject.
For an African-American man (self-reported), R is replaced by 1.
For others, R is replaced by 0.
A1 and A2: represent the age of the subject.
For an individual that is less than 55 years of age, A1 is replaced by zero and A2 is replaced by zero.
For an individual between the ages of 55 and 65 years, A1 is replaced by 1 and A2 is replaced by zero.
For an individual that is older than 65, A1 is replaced by zero and A2 is replaced by 1.
B: represents the body mass index of the individual at the time of the diagnosis.
For an individual with a BMI equal or above 30 kg/m², B is replaced by 1.
For an individual with a BMI of less than 30 kg/m², then B is replaced by 0.
PSA$_i$: represents the baseline/initial PSA measure of the individual (generally at 50 years of age, but not limited thereto).
X: represents the time at which the PSA measure was taken in relation to diagnosis of prostate cancer or the confirmation of the absence of prostate cancer for a representative population.

Low-Risk Prostate Cancer Reference PSA Growth Curve:
For X<2.78

$$PSA_j = 0.16 + (0.02*R) + (0.1*A1) + (0.12*A2) + (-0.03*B) + (1.22*PSA_i) + [(0.04 + (0.07*A1) + (0.012*A2) + (0.03*PSA_i))]*(2.78-X)$$

For X≥2.78

$$PSA_j = [0.16 + (0.02*R) + (0.1*A1) + (0.12*A2) + (-0.03*B) + (1.22*PSA_i)]* e^{(0.16 + (-0.03*R) + (-0.07*A1) + (0.04*A2))*(X-2.78)}$$

in which the coefficients are as described above.

High-Risk Prostate Cancer Reference PSA Growth Curve:
For X<5.64

$$PSA_j = 0.21 + (0.02*R) + (0.1*A1) + (0.12*A2) + (-0.03*B) + (1.22*PSA_i) + [(0.08 + (0.01*A1) + (0.012*A2) + (0.03*PSA_i))]*(5.64-X)$$

For X≥5.64

$$PSA_j = [0.21 + (0.02*R) + (0.1*A1) + (0.12*A2) + (-0.03*B) + (1.22*PSA_i)]* e^{(0.34 + (-0.03 + (-0.03*R) + (-0.07*A1) + (0.04*A2))*(X-5.64)}$$

In which the coefficients are as described above,

Utilizing the above functions, the individualized reference PSA growth curves can be generated for PSA vs. time.

In conjunction with the development of the individualized reference PSA growth curves, the multiple individual PSA levels that have been obtained for the individual can be utilized to generate two different possible PSA/time relationship models for the individual.

The first model is a linear model in which the function can be described as:

$$PSA = \beta_o + \beta_t * time$$

The second model is an exponential model in which the function can be described as:

$$PSA = \beta_o * e^{\beta_t t}$$

In which
$\beta_o$ represents the intercept of the line that describes the relationship between PSA and time. Clinically it is an estimate of the baseline PSA measures (that is the value of PSA at time (zero),
$\beta_t$ is the slope of the linear (1st model) or the exponential (second model) line that describes the relationship between PSA and time. Known also as the linear beta coefficient (1st model) or exponential coefficient (second model).

These two models can be developed using standard statistical regression methodology. For instance, in one embodiment statistical regression software such as SAS® or R® can be utilized. The statistical regression methodology can utilize any appropriate process (for example, the function/procedure NlIN) to fit the model and estimate the unknown parameter/coefficients.

Following development of the two different possible models (linear or exponential), the best fitted model can be evaluated to determine which of the three possible scenarios (non-cancerous, low-risk cancer, or high-risk cancer) the individual's best-fitted model is most accurate. In general the best-fitted model can be determined by use of the R-squared measure as is known in the art. According to known statistical processes, the R-squared measure can be evaluated as:

$$R^2 = \frac{SSR}{SST} = \frac{\sum (\hat{y}_i - \bar{y})^2}{\sum (y_i - \bar{y})^2}$$

In which
SSR represents the residuals sum of squares
SST represents the total sum of squares Having the best-fitted model for the individual based upon the individual's own PSA levels and the risk profile data of the individual, the PSA rate of change for that individual can then be determined as the $1^{st}$ derivative of the best-fitted line (i.e., the rate of change of the PSA level vs. time curve as determined for that individual). In particular, if the best fitted model for the individual is the linear model, then the PSA rate will be:

PSA rate=$\beta_t$ and the parameter $\beta_t$ is estimated through the linear regression model.

Alternatively, if the best fitted model for the individual is the exponential model, then the PSA rate will be:

PSA rate=$\beta_o * e^{\beta t}$

Having thus established the individualized PSA rate of change for the subject, the PSA rate can be compared to a threshold value, with a high rate of change in PSAV indicating that the subject has a high probability of being afflicted with high-risk, aggressive prostate cancer and should be further treated, for instance through undergoing a biopsy. On the other hand, if the individual's PSA rate of change is determined to be lower than the threshold value, the subject has a low probability of having aggressive cancer, and most likely is afflicted at most with low-risk, non-aggressive prostate cancer. In such a situation, further invasive treatment is not called for, and the subject can be merely monitored with future PSA level determination.

The threshold value for determining prostate cancer probability can vary, primarily depending upon the individual's race. For instance, If the subject at the time of the 1st given PSA level is older than 50 years of age, is African American, and the rate of change of PSA as determined as described herein is 0.22 ng/ml/year or greater, the subject can have a high probability of high-risk prostate cancer and should be subjected to further testing and/or treatment. For instance, in this situation, the subject can undergo a biopsy.

If, on the other hand, the subject at the time of the $1^{st}$ given PSA level is older than 50 years of age, and the subject is not African American, then the threshold rate can be higher. For instance, in this situation if the rate of change of PSA in the subject is about 0.37 ng/ml/year or greater, then subject is thought to have a high probability of high-risk prostate cancer.

The present disclosure may be better understood with reference to the Example set forth below.

EXAMPLE 1

Non-linear mixed model methods were used to describe, quantify, and compare the trajectory of PSA change over time among three groups of men (study groups): men with no evidence of prostate cancer, men diagnosed with low-risk prostate cancer and men diagnosed with high-risk prostate cancer using data from the Prostate, Lung, Colorectal and Ovarian Cancer Screening Trial (PLCO).

Material and Methods

Using data from the PLCO clinical trial, analyses were conducted retrospectively "following" each individual's repeated PSA measures over time till they were confirmed either to have high-risk, low-risk cancer or exited the study without a cancer diagnosis.

The analysis was conducted using data from 38,340 men randomized into the Prostate cancer screening arm of the PLCO trial. Briefly, each man was expected to comply with up to 6 six annual blood draws and digital rectal examination (DRE) during the initial six years of active screening, after which they were passively followed for an additional seven years.

Included were men between 50-75 years of age at baseline who had at least four PSA measures. Potential sources of misclassification were excluded: men with reported unconfirmed diagnosis of prostate cancer, those who were classified as non-responsive or loss of follow up; those who did not have complete diagnostic/biopsy information in response to a positive screening. We also excluded men with BPH at baseline or those with incomplete information of baseline age, BMI or race (FIG. 5 illustrates the cohort selection tree).

The classification of prostate cancer into high/low biological risk was based on the prognostic stage introduced by The American Joint Committee on Cancer (AJCC) in 2010. Any Prostate cancer that met one of these criteria was considered high biological risk: PSA level ≥20 ng/ml prior to diagnosis, cancer that had invaded prostate capsule, Prostate cancer that involves more than one lobe, or Gleason score (if available) >7; all other prostate cancers were considered of low biological risk (prognostic group IIa and below).

Initially, individual and mean trajectories of PSA were observed by plotting PSA as a function of time for each study group (using a "spaghetti plot" for individual curves and locally weighted scatter plot smoothing regression for the mean trajectory). These graphical tools were used to explore suitable functions of PSA change pattern. The observed plots supported prior observations that PSA levels increase with age/time and that this change is not always constant (i.e., is not linear-monotonic) especially among prostate cancer group starting sometime close to diagnosis. To account for this pattern, multiphase non-linear mixed models were used to estimate PSA change over time:

According to a linear-exponential piecewise PSA model, the individual PSA as a function of time (years) from diagnosis or exit was estimated. It was hypothesized that each individual's PSA trajectory started with a phase of slow linear change followed by a phase of rapid exponential increase. The transition point from the linear phase to exponential phase was considered unknown and unique for each individual influenced by random factors; we called this transition point the change point (CP).

The model was built in two stages:

1. Because the hypothesis was that the pattern of change in PSA is significantly different for healthy men compared to men in the two cancer groups—different coefficient estimates were allowed per each of the 3 groups. An initial model used an interaction term between the group type and time. To account for individual-level natural heterogeneity for rate of growth, change point and intercept, we included random effects for their corresponding parameter estimates. The most parsimonious model was determined by backwards elimination of non-significant terms. As expected, cancer groups exhibited a significant exponential stage. The estimate of CP for the non-cancer group was significantly low (very close to zero) compared to significant values for cancer groups.

2. A reduced model was then used (allowing transition to an exponential phase among the cancer groups only) to establish the PSA growth curve and estimate average PSAV as ng/ml/year per group while adjusting for baseline age, BMI ($kg/m^2$), PSA measure (ng/ml) and race (African American (AA) versus others). To investigate and account for possible effect-modification of these variables on PSA change over time, an interaction term was included between these variables and time, According to a Linear-Linear piecewise LOG PSA model, the change of PSA over time was estimated on the natural log transformed scale of the PSA measures. Individual log [PSA+1] was regressed as a function of time (years to diagnosis/exit). This transformation improved the distribution of the data, allowed a realistic linear assumption of time—PSA relationship and represented PSA change over time as an annual percent rate (change) instead of an absolute change, replaced the observed linear-exponential relationship by linear-linear, and simplified derivation to allow for a single growth rate for all years post the CP. This model was used in two stages as follows:

1. An initial model was built that allowed the same function for all groups. A linear-linear multiphase model was used with unknown continuous CP. Fixed and random effects were included to estimate the mean, and allow for individual variation on the intercept, time coefficients and the CP. The most parsimonious model was chosen by backwards elimination of non-significant terms. The cancer groups exhibited a significant second time coefficient that was not significant in the non-cancer group.

2. The reduced model was then proposed to describe growth of log (PSA+1) as a function of time to exit while adjusting for potential confounders allowing a transition to a second linear phase among the cancer groups only.

In all models, the transition from one phase to another was assumed to be continuous so that even though there is a shift in function, the changeover to the new section is steady and incremental. PSA change over time (PSA rate) was estimated by taking the 1st derivative of the final equation in each model. The models included time variables, main effects of baseline characteristics, and corresponding interactions with the time variables (at the two phases). The time variable corresponded to PSA slope; and interaction of time with baseline characteristics corresponded to the influence of these characteristics on PSA slope/change. All the analysis was done on SAS® 9.4 (Cary, N.C.) with significance level of 0.05.

Results 20,888 men met the exclusion/inclusion criteria. Table 1 below reports the baseline characteristics for the three study groups; chi-squared tests and two-sided t-tests were used for statistical comparisons. Men with diagnosis of prostate cancer (both high and low-risk) compared to healthy men were found to be older at baseline, have shorter follow-up, higher PSA measures at baseline, fewer PSA measurements, and a shorter period between last PSA test and study exit. AA men and men with family history of prostate cancer were more likely to be diagnosed with prostate cancer. Men with high-risk prostate cancer (HRC) were found comparable to low-risk prostate cancer (LRC)—except for longer duration of follow-up and longer time between the last PSA and exit day.

TABLE 1

| | Men with no cancer (19,196) | Men with LRC* (1368) | Men with HRC** (324) | Comparison (p-value for difference between study groups by characteristic) | | |
|---|---|---|---|---|---|---|
| | | | | No cancer vs. LRC | No cancer vs. HRC | LRC vs. HRC |
| Race, n (%) | | | | | | |
| African American | 742 (90.05) | 62 (7.52) | 20 (2.43) | 0.098 | 0.03 | 0.2 |
| Others | 18454 (91.98) | 1306 (6.51) | 304 (1.52) | | | |
| Ethnicity, n (%) (missing = 606) | | | | | | |
| non-Hispanic | 18203 (91.84) | 1310 (6.61) | 308 (1.55) | 0.32 | 0.88 | 0.74 |
| Hispanic | 428 (92.84) | 26 (5.64) | 7 (1.52) | | | |
| Family history, n (%) (missing = 144) | | | | | | |
| No | 17773 (91.33) | 1225 (7.06) | 284 (1.62) | <0.001 | <0.001 | 0.33 |
| Yes, immediate family member | 1291 (87.09) | 132 (9.96) | 39 (2.94) | | | |
| Age, n (5) (years) | | | | | | |
| <=55, n = 2,228 | 2096 (94.08) | 107 (4.8) | 25 (1.12) | 0.0004 | 0.006 | 0.34 |
| 55-65, n = 13,658 | 12560 (91.96) | 898 (6.57) | 200 (1.46) | | | |
| >65, n = 5002 | 4540 (90.76) | 363 (26.54) | 99 (1.96) | | | |
| Mean (95% CI) | 61.42 (61.34-61.49) | 62.21 (61.96-62.46) | 62.73 (62.17-63.29) | <0.001 | <0.001 | 0.08 |

TABLE 1-continued

|  | Men with no cancer (19,196) | Men with LRC* (1368) | Men with HRC** (324) | No cancer vs. LRC | No cancer vs. HRC | LRC vs. HRC |
|---|---|---|---|---|---|---|
| BMI, n (%) | | | | | | |
| <=30 kg/m2 | 14431 (91.58) | 1068 (6.78) | 258 (1.64) | 0.016 | 0.0655 | 0.5399 |
| >30 kg/m2 | 4765 (92.87) | 300 (5.85) | 66 (1.29) | | | |
| Mean (95% CI) | 27.75 (27.67-27.81) | 27.34 (27.14-27.54) | 27.63 (27.22-28.05) | <0.001 | 0.6 | 0.20 |
| PSA at baseline (ng/ml) mean/median (95% CI) | 1.05/1.06 (1.04-1.06) | 2.51/2.16 (2.42-2.59) | 2.91/1.94 (2.37-3.46) | <0.001 | <0.001 | 0.14 |
| Years of follow up (years) mean/median (95% CI) | 11.49/11.51 (11.46-11.52) | 7.52/7.47 (7.37-7.66) | 8.24/7.85 (7.54-8.16) | <0.001 | <0.001 | 0.053 |
| Number of PSA tests mean/median (95% CI) | 5.59/6.00 (5.58-5.60) | 5.28/6.00 (5.24-5.33) | 5.21/5.00 (5.12-5.30) | <0.001 | <0.001 | 0.16 |
| Years from last PSA to exit or diagnosis mean/median (95% CI) | 6.56/7.17 (6.54-6.59) | 2.92/2.57 (2.79-3.04) | 3.36/3.32 (3-07-3.64) | <0.001 | <0.001 | 0.005 |

*LRC: Low-risk prostate cancer
**HRC: high-risk prostate cancer

FIG. 2, FIG. 3, and FIG. 4 illustrate the observed trajectory of the three groups separately. For men in the non-cancer group (FIG. 2), a linear trend, slightly increasing was observed. A similar linear pattern was observed among the two cancer groups, but only during the initial years of follow-up. Among the low-risk cancer group (FIG. 3), the linear phase changed to exponential phase about 2-3 years before diagnosis. The linear-exponential pattern is more pronounced among high-risk cancer patients (FIG. 4) and the CP takes place earlier; around 4-5 years before diagnosis. Table 2 below reports the unique CP statistics for the two cancer groups estimated from the final reduced models.

TABLE 2

| Model | Outcome | Function | Group | Change point summary Mean (95% CI) | Median ($25^{th}$, $75^{th}$) |
|---|---|---|---|---|---|
| Annual PSA rate | PSA | Linear-exponential | Low-risk prostate cancer | 2.58 (2.58, 2.58) | 2.62 (2.31, 3.02) |
| | | | High-risk prostate cancer | 5.21 (4.85, 5.58) | 5.24 (4.75, 5.59) |
| Annual % PSA rate model | Log PSA | Linear-linear | Low-risk prostate cancer | 2.00 (2.00, 2.00) | 2.00 (2.00 2.00) |
| | | | High-risk prostate cancer | 3.96 (3.61, 4.31) | 3.96 (3.70 3.97) |

Table 3 below summaries PSA change/rate over time using different methods, the first (Arithmetic velocity) is derived from a traditional formula for PSAV:

$$((1/n-1))*(\Sigma_{i=1}^{n}(p_i-p_{i-1})/(t_i-t_{i-1})).$$

where n=total number of PSA tests
p=PSA value
t=time at PSA test)

while the others are derived from the disclosed model obtained by taking the $1^{st}$ derivative at a fixed point before diagnosis.

TABLE 3

| Method | Men with no cancer (19196) mean (95% CI) | Men with LRC (1368) mean (95% CI) | Men with HRC (324) Mean (95% CI) | No cancer vs. LRC | No cancer vs. HRC | LRC vs. HRC |
|---|---|---|---|---|---|---|
| Arithmetic velocity (ng/ml/year) | 0.06 (0.06-0.07) | 0.37 (0.34-0.39) | 0.79 (0.55-1.03) | <0.001 | <0.001 | <0.001 |
| Annual rate before change point (ng/ml/year) | 0.05 (0.05-0.05) | 0.16 (0.15-0.17) | 0.13 (0.11-0.16) | <0.001 | <0.001 | 0.21 |
| Annual rate after change point (1 years before diagnosis) ng/ml/year | 0.05 (0.05-0.05) | 0.59 (0.52-0.66) | 2.60 (2.11-3.09) | <0.001 | <0.001 | <0.001 |

TABLE 3-continued

|  | Men with no cancer (19196) mean (95% CI) | Men with LRC (1368) mean (95% CI) | Men with HRC (324) Mean (95% CI) | Comparison (p-valued for difference between study groups) | | |
|---|---|---|---|---|---|---|
| Method |  |  |  | No cancer vs. LRC | No cancer vs. HRC | LRC vs. HRC |
| Annual % PSA rate before change point | 1.63% (1.57%-1.68%) | 5.56% (5.33%-5.78%) | 5.06% (4.54%-5.57%) | <0.001 | <0.001 | 0.31 |
| Annual % PSA rate after change point | 1.63% (1.57%-1.68%) | 10.85% (9.02%-12.68%) | 12.10% (10.3%-14.17%) | <0.001 | <0.001 | 0.09 |

Men who were diagnosed with high-risk prostate cancer had a statistically significant higher estimate of absolute PSA change over time across different methods of estimation. The annual percent (%) rate is higher among men who developed prostate cancer but was comparable between high-risk and low-risk prostate cancer. PSA annual change estimated by the models illustrated a narrower 95% CI (less variability around the mean values). Also, traditional methods did not capture $2^{nd}$ order effects of PSA exponential growth after CP, while the disclosed model can. This is crucially important as it is necessary to differentiate high-risk prostate cancer from low-risk prostate cancer in order to provide appropriate care (i.e., treating individuals with indolent cancer much less aggressively).

Table 4, below, shows PSA rate of change and annual % PSA at one year prior to diagnosis/exit. These rates are illustrated for all study groups, stratified by age and race and adjusted for baseline distribution of BMI and initial PSA value of 1.3 ng/ml. After the CP and at one year prior to diagnosis/exit, the absolute PSA rate among men in the high-risk cancer group appeared to be significantly greater compared to no-cancer and low-risk groups. The annual percent (%) rate was higher among men who developed prostate cancer but the difference between high-risk and low-risk groups was not as wide.

TABLE 4

| Race | Age | Group | MEAN | (95% CI) | Median | $25^{TH}$ Percentile | $75^{TH}$ percentile |
|---|---|---|---|---|---|---|---|
| Estimated annual PSA rate 1 year prior to exit stratified by race, age and study groups and fixed at baseline BMI of 25 and initial PSA of 1.3 | | | | | | | |
| Non-African American | Youngest (<55) | No cancer | 0.05 | (0.04 0.05) | 0.04 | 0.02 | 0.06 |
|  |  | Low-risk cancer | 0.65 | (0.53 0.77) | 0.69 | 0.58 | 0.88 |
|  |  | High-risk cancer | 2.82 | (2.08 3.56) | 1.95 | 1.63 | 3.57 |
|  | Middle (55-65) | No cancer | 0.05 | (0.05 0.05) | 0.04 | 0.02 | 0.07 |
|  |  | Low-risk cancer | 0.47 | (0.41 0.54) | 0.55 | 0.42 | 0.71 |
|  |  | High-risk cancer | 2.10 | (1.65 2.54) | 1.88 | 1.25 | 2.68 |
|  | Older (65≥) | No cancer | 0.06 | (0.05 0.06) | 0.04 | 0.02 | 0.07 |
|  |  | Low-risk cancer | 0.92 | (0.79 1.06) | 1.07 | 0.81 | 1.40 |
|  |  | High-risk cancer | 4.30 | (3.50 5.11) | 4.21 | 2.88 | 6.33 |
| African Americans | Youngest (<55) | No cancer | 0.05 | (0.04 0.07) | 0.04 | 0.03 | 0.05 |
|  |  | Low-risk cancer | 0.69 | (0.50 0.88) | 1.21 | 0.81 | 1.26 |
|  |  | High-risk cancer | 3.04 | (2.04 4.05) | 1.90 | 1.89 | 1.91 |
|  | Middle (55-65) | No cancer | 0.06 | (0.05 0.07) | 0.04 | 0.03 | 0.07 |
|  |  | Low-risk cancer | 0.51 | (0.36 0.65) | 0.70 | 0.50 | 0.94 |
|  |  | High-risk cancer | 2.26 | (1.60 2.93) | 2.50 | 1.75 | 3.71 |
|  | Older (65≥) | No cancer | 0.06 | (0.05 0.07) | 0.04 | 0.03 | 0.07 |
|  |  | Low-risk cancer | 0.98 | (0.73 1.22) | 1.00 | 0.78 | 1.54 |
|  |  | High-risk cancer | 4.62 | (3.28 5.95) | 3.82 | 2.11 | 4.09 |
| Estimated annual % PSA rate 1 year prior to exit stratified by age, race, study group and fixed at baseline BMI of 25 and initial PSA of 1.3 | | | | | | | |
| Non-African American | Youngest (<55) | No cancer | 1.48% | (1.32% 1.64%) | 11.91% | 10.62% | 13.77% |
|  |  | Low-risk cancer | 11.67% | (8.96% 14.38%) | 12.20% | 11.25% | 13.60% |
|  |  | High-risk cancer | 12.91% | (10.01% 15.81%) | 13.21% | 11.34% | 15.39% |
|  | Middle (55-65) | No cancer | 1.61% | (1.55% 1.68%) | 11.88% | 10.39% | 13.76% |
|  |  | Low-risk cancer | 10.53% | (8.64% 12.42%) | 11.52% | 10.25% | 13.07% |
|  |  | High-risk cancer | 11.79% | (9.66% 13.91%) | 12.56% | 10.81% | 14.37% |
|  | Older (65≥) | No cancer | 1.68% | (1.57% 1.78%) | 11.87% | 10.39% | 13.76% |
|  |  | Low-risk cancer | 10.93% | (8.61% 13.26%) | 11.81% | 10.53% | 13.33% |
|  |  | High-risk cancer | 12.18% | (9.68% 14.68%) | 12.80% | 11.08% | 14.18% |
| African Americans | Youngest (<55) | No cancer | 1.82% | (1.53% 2.12%) | 11.85% | 10.62% | 13.25% |
|  |  | Low-risk cancer | 14.11% | (10.31% 17.91%) | 15.55% | 14.43% | 17.81% |
|  |  | High-risk cancer | 15.31% | (11.52% 19.10%) | 9.36% | 4.67% | 14.04% |
|  | Middle (55-65) | No cancer | 1.96% | (1.70% 2.21%) | 11.72% | 10.33% | 13.53% |
|  |  | Low-risk cancer | 13.00% | (9.62% 16.39%) | 13.92% | 12.75% | 15.88% |
|  |  | High-risk cancer | 14.22% | (10.87% 17.57%) | 15.93% | 10.33% | 20.55% |
|  | Older (65≥) | No cancer | 2.02% | (1.75% 2.29%) | 11.80% | 10.46% | 13.90% |
|  |  | Low-risk cancer | 13.40% | (9.78% 17.01%) | 15.77% | 13.52% | 17.58% |
|  |  | High-risk cancer | 14.61% | (11.04% 18.18%) | 13.64% | 4.26% | 13.91% |

As shown, the linear-exponential piecewise model and linear-linear piecewise model can parsimoniously describe the absolute and relative (%) change of PSA among men diagnosed with high-risk prostate cancer, low-risk prostate cancer or not diagnosed with prostate cancer. Both models include random components for natural heterogeneity between individuals and control for factors that may affect PSA. Across all groups of age, race, BMI and initial PSA and in both models, patients who were ultimately diagnosed with high-risk prostate cancer had a PSA change profile that appeared distinct starting as early as 5 to 2 years prior to date of diagnosis; while both cancer groups demonstrated an inflection in PSA trajectories transitioning from a linear into an exponential pattern. Further, the low-risk cancer group had a less aggressive exponential pattern with the CP being much closer to diagnosis compared to high-risk cancer. When examining rate of PSA change one year prior to exit, it was found that men in the high-risk cancer group had much higher absolute PSA rate compared to other two groups.

Using the disclosed method to quantify PSA velocity/rate, identification of a distinct range for calculated rates is possible when considering high-risk cancer as compared to low-risk cancer and no cancer. Most past studies have estimated the individual velocities using a linear model (mostly one phase and sometimes two phases) within a narrow time frame, using few PSA measures in close intervals. The disclosed model is flexible as it does not assume a monotonic rate of change and accounts for the actual pattern of PSA trajectory, uses multiple (e.g., 5-6) PSA measures taken across a time frame of 1-14 years, accounts for baseline characteristics and has been developed by use of a large enough sample size to control for within-individual variations.

The disclosed PSA growth model provides a mathematical representation of the natural progression of prostate cancer and illustrates a clear distinction in PSA rate and pattern among those diagnosed with high-risk prostate cancer when compared to low-risk prostate cancer and no-cancer groups. Moreover, this clear distinction takes place within a window of time before typical clinical diagnosis that it is relevant to early detection.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for determination of the risk of aggressive prostate cancer in a subject, the method comprising:
    obtaining three or more PSA concentration levels from the subject, the PSA concentration levels being obtained at times spaced apart from one another;
    generating a no cancer scenario PSA level growth curve, a low-risk cancer scenario PSA level growth curve, and a high-risk cancer scenario PSA level growth curve for the subject,
    wherein the no cancer scenario PSA level growth curve is generated by the following function:

$$PSA_j=0.7+(0.07*R)+(0.07*A1)+(0.11*A2)+(-0.03*B)+(0.85*PSA_j)+[(0.05+(0.01*R)+(0.1*A2))*(X)];$$

the low-risk cancer scenario PSA level growth curve is generated by the following function:
for X<2.78

$$PSA_j=0.16+(0.02*R)+(0.1*A1)+(0.12*A2)+(-0.03*B)+(1.22*PSA_j)+[(0.04+(0.07*A1)+(0.012*A2)+(0.03*PSA_j))]*(2.78-X)$$

for X>2.78

$$PSA_j=[0.16+(0.02*R)+(0.1*A1)+(0.12*A2)+(-0.03*B)+(1.22*PSA_j)]*e^{(0.16+(-0.03*R)+(-0.07*A1)+(0.04*A2))*(X-2.78)}$$

and the high-risk scenario PSA level growth curve is generated by the following function:
for X<5.64

$$PSA_j=0.21+(0.02*R)+(0.1*A1)+(0.12*A2)+(-0.03*B)+(1.22*PSA_j)+[(0.08+(0.01*A1)+(0.012*A2)+(0.03*PSA_j))]*(5.64-X)$$

for X>5.64

$$PSA_j=[0.21+(0.02*R)+(0.1*A1)+(0.12*A2)+(-0.03*B)+(1.22*PSA_j)]*e^{(0.34+(-0.03)+(-0.03*R)+(-0.07*A1)+(0.04*A2))*(X-5.64)}$$

wherein;
    $PSA_j$ is the PSA concentration level at a time point j,
    R=1 if the subject is self-reported African American, R=2 for others,
    A1=0, A2=0 if the subject is less than 55 years of age,
    A1=1, A2=0 if the subject is between the ages of 55 and 65 years
    A1=1, A2=1 if the subject is older than 65,
    B=1 if the subject has a BMI equal or above 30 kg/m$^2$,
    B=0 if the subject has a BMI of less than 30 kg/m$^2$,
    $PSA_j$ is the earliest PSA concentration level of the subject,
    X=the time in years between obtaining a PSA concentration level and the diagnosis of prostate cancer or confirmation of the absence of prostate cancer for a population representative of the subject;
modeling by use of the three or more PSA concentration levels a first PSA/time relationship based upon a linear PSA growth curve and a second PSA/time relationship based upon an exponential PSA growth curve;
carrying out a regression on each of the first and second PSA/time relationship models to determine which relationship model is the best fitted model of three or more PSA concentration levels;
determining which of the PSA level growth curves best describes the best fitted model and thereby determining that the best fitted model describes a no cancer scenario growth curve, a low-risk cancer scenario growth curve, or a high-risk cancer scenario growth curve for the subject;
using the best fitted model, obtaining the PSA rate of change for the subject through determination of the derivative of the best fitted model; and
comparing the PSA rate of change for the subject thus obtained to a threshold value for the subject; wherein upon a finding that the PSA rate of change for the subject is greater than the threshold value and that the best fitted model describes a high-risk cancer scenario growth curve for the subject, the subject is determined to be at high risk of aggressive prostate cancer; and
carrying out a prostate biopsy out on the subject upon said determination.

2. The method of claim 1, wherein the subject is asymptomatic for prostate cancer.

3. The method of claim 1, wherein the three or more PSA concentration levels are obtained at times spaced apart from one another of about six months or greater.

4. The method of claim 1, wherein the three or more PSA concentration levels are obtained at times spaced apart from one another of from about six months to about three years.

5. The method of claim 1, wherein the first PSA/time relationship model based upon the linear PSA growth curve is described by the following statistical regression function:

$$PSA=\beta_o+\beta_t*time$$

wherein
- $\beta_o$ represents the intercept of the line that describes the relationship between PSA and time; and
- $\beta_t$ is the slope of the linear growth curve that describes the relationship between PSA and time.

6. The method of claim 1, wherein the second PSA/time relationship model based upon the exponential growth curve is described by the following statistical regression function:

$$PSA=\beta_o*e^{\beta_t t}$$

wherein
- $\beta_o$ represents the intercept of the line that describes the relationship between PSA and time; and
- $\beta_t$ is the slope of the exponential growth curve that describes the relationship between PSA and time.

7. The method of claim 1, wherein the best fitted model is determined by use of an R-squared measure.

8. The method of claim 7, wherein the R-squared measure is evaluated by the following relationship:

$$R^2 = \frac{SSR}{SST} = \frac{\sum (\hat{y}_i - \bar{y})^2}{\sum (y_i - \bar{y})^2}.$$

9. The method of claim 1, wherein upon a determination that the best fitted model is the first PSA time relationship model, the PSA rate of change for the subject is determined to be equivalent to $\beta_t$ wherein
- $\beta_t$ is a slope of a linear growth curve that describes the relationship between PSA and time.

10. The method of claim 1, wherein upon a determination that the best fitted model is the second PSA time relationship model, the PSA rate of change for the subject is determined to be equivalent to $\beta_o*e^{\beta t}$ wherein
- $\beta_o$ represents the intercept of a line that describes the relationship between PSA and time; and
- $\beta_t$ is a slope of the exponential curve that describes the relationship between PSA and time.

11. The method of claim 1, wherein the threshold value is 0.22 ng/ml/year when the subject is over 50 years of age and African American.

12. The method of claim 1, wherein the threshold value is 0.37 ng/ml/year when the subject is over 50 years of age and is not African American.

\* \* \* \* \*